(12) United States Patent
Kondoh

(10) Patent No.: US 8,574,159 B2
(45) Date of Patent: Nov. 5, 2013

(54) THERMALLY ENHANCED ULTRASONIC PROBE

(75) Inventor: Takashi Kondoh, Saitama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 861 days.

(21) Appl. No.: 11/825,781

(22) Filed: Jul. 9, 2007

(65) Prior Publication Data

US 2008/0009742 A1 Jan. 10, 2008

(30) Foreign Application Priority Data

Jul. 10, 2006 (JP) .................. 2006-189749

(51) Int. Cl.
*A61B 8/14* (2006.01)
*H01L 41/083* (2006.01)

(52) U.S. Cl.
USPC .......... 600/459; 310/311; 310/334; 310/341; 310/346

(58) Field of Classification Search
None
See application file for complete search history.

(56) References Cited

U.S. PATENT DOCUMENTS

| | | | | |
|---|---|---|---|---|
| 5,545,942 A * | 8/1996 | Jaster et al. | .................. | 310/341 |
| 5,721,463 A * | 2/1998 | Snyder | ......................... | 310/334 |
| 6,443,900 B2 * | 9/2002 | Adachi et al. | ................ | 600/458 |
| 6,445,580 B1 * | 9/2002 | Cohen et al. | ............. | 361/679.47 |
| 6,546,080 B1 * | 4/2003 | Geitz | ............................. | 378/141 |
| 2004/0002655 A1 * | 1/2004 | Bolorforosh et al. | ......... | 600/459 |
| 2005/0043628 A1 * | 2/2005 | Baumgartner et al. | ....... | 600/459 |
| 2006/0235300 A1 * | 10/2006 | Weng et al. | ................... | 600/439 |
| 2007/0049829 A1 * | 3/2007 | Kaminski et al. | ............. | 600/459 |
| 2007/0167803 A1 * | 7/2007 | Kaminski et al. | ............. | 600/459 |
| 2007/0276248 A1 * | 11/2007 | Saito et al. | .................... | 600/459 |
| 2008/0139945 A1 * | 6/2008 | Hu | ................. | 600/459 |
| 2008/0188755 A1 * | 8/2008 | Hart | ............................. | 600/459 |
| 2008/0262358 A1 * | 10/2008 | Kaminski et al. | ............. | 600/459 |

FOREIGN PATENT DOCUMENTS

| | | |
|---|---|---|
| EP | 1 671 588 A1 | 6/2006 |
| JP | 03-203290 | 9/1991 |
| JP | Hei03-122807 | 12/1991 |

(Continued)

OTHER PUBLICATIONS

European Search Report dated Oct. 29, 2007.

(Continued)

*Primary Examiner* — Long V. Le
*Assistant Examiner* — Angela M Hoffa
(74) *Attorney, Agent, or Firm* — Edwards Wildman Palmer LLP; Scott D. Wofsy; David J. Silva

(57) ABSTRACT

The present invention relates to an ultrasonic probe provided with a piezoelectric element for ultrasonic generation that has drive electrodes formed on two main surfaces thereof; an acoustic matching layer formed on the first main surface side of the piezoelectric element; a backing member attached to the second main surface side of the piezoelectric element; a base for heat dissipation provided on a lower surface of the backing member; and a thin metal plate for heat transfer that is thermally bonded between at least one of the main surfaces of the piezoelectric element and the base for heat dissipation; wherein the thin metal plate for heat transfer is surface-bonded to extend from one end of the piezoelectric element over the center thereof toward the other end. This configuration ensures that heat generated by the electrical-mechanical conversion of the piezoelectric element is transferred away in a satisfactory manner, enabling suppression of any temperature rise in the piezoelectric element.

6 Claims, 4 Drawing Sheets

(56) References Cited

FOREIGN PATENT DOCUMENTS

| | | |
|---|---|---|
| JP | 05-244690 | 9/1993 |
| JP | 07-265315 | 10/1995 |
| JP | 11-309143 | 11/1999 |
| WO | WO2005/030055 A1 | 4/2005 |

OTHER PUBLICATIONS

Office Action issued by the Japanese Patent Office on May 23, 2011.
Office Action issued by the Japanese Patent Office on Dec. 9, 2010 of the priority patent application No. JP2006-189749, along with the translation and verification of translation.

\* cited by examiner

THERMALLY ENHANCED ULTRASONIC PROBE

BACKGROUND OF THE INVENTION

The present invention relates to an ultrasonic probe in which any rise in temperature of the piezoelectric element that acts as an ultrasonic generation source is suppressed, and, in particular, to an ultrasonic probe in which the effect of suppressing such a temperature rise is increased.

Since an ultrasonic probe (piezoelectric element) generates heat while converting electrical energy into mechanical oscillation energy, this can lead to problems such as a reduction in reliability due to a lack of strength caused by thermal deterioration of materials, or a reduction in quality due to changes in the characteristics. In addition, an ultrasonic probe for medical purposes could cause safety problems, such as low-temperature burning of the skin of a living body. There are examples in the prior art of measures taken to solve these problems, such as those disclosed in the Japanese Patent Laid-Open Publication No. 5-244690 and Japanese Patent Laid-Open Publication No. 3-203290 of the present inventor, as will be described below.

DESCRIPTION OF RELATED ART

A prior-art of this type of ultrasonic probe is shown in FIG. 4, where FIG. 4A is a partial section of the probe in the long-axis direction with the case thereof removed and FIG. 4B is a section taken along the short-axis direction thereof.

In this ultrasonic probe, a plurality of piezoelectric elements 1 of a narrow card shape are arrayed in the widthwise direction thereof and are disposed in an array on a backing member 2, as shown in FIG. 4A. In this case, the widthwise direction of the piezoelectric elements 1 is taken to be the long-axis direction of the ultrasonic probe (the longitudinal direction shown in FIG. 4A) and the longitudinal direction thereof is taken to be the short-axis direction. The piezoelectric elements 1 are subjected to sector drive or linear drive in the long-axis direction, by way of example.

The piezoelectric elements 1 have drive electrodes 3a and 3b on two main surfaces thereof, and the drive electrodes 3a that are disposed on the main surface that acts as an ultrasonic transceiver surface are grounded to provide a ground potential. The drive electrodes 3b that are disposed on the second main surface on the backing member 2 side have a pulse voltage applied continuously thereto. Note that the drive electrodes 3a disposed on first main surface are taken to be ground electrodes 3a while the drive electrodes 3b disposed on the second main surface are taken to be signal electrodes 3b, for the sake of convenience in this case. Since this brings the ground electrode 3a side into contact with the living body, safety is improved. In addition, the signal electrodes 3b obtain an electrical signals based on the reflected waves from the body.

In this case, the signal electrodes 3b disposed on the second main surface are in contact with signal paths 4a of a flexible substrate 4 that is provided between the two ends of the piezoelectric elements 1 and the backing member 2, and are led out in a zigzag fashion. The ground electrodes 3a on the first main surface are connected in common by means such as a conducting wire 5 that extends over the plurality of piezoelectric elements 1 at the other end of the piezoelectric elements 1, and are connected to a ground path (not shown in the figures) of the flexible substrate 4.

Alternatively, a thin metal plate (not shown in the figures) formed of silver (Ag) is interposed between the signal electrodes 3b and the backing member 2, and the signal electrodes 3b are connected by conducting wires to the corresponding signal lines of the flexible substrate 4. In such a case, the thin metal plate is more flexible than the flexible substrate 4, so that mechanical deformation with respect to the piezoelectric elements 1 is restrained and the oscillation characteristics thereof are improved (refer to paragraphs [0004] to [0005] of Japanese Patent Laid-Open Publication No. 11-309143).

Ordinarily, an acoustic matching layer 6 and also an acoustic lens 7 are provided superimposed on the first main surface of the piezoelectric elements 1, as shown in FIG. 4B. The acoustic matching layer 6 is designed to adjust the acoustic impedance between the piezoelectric elements 1 and the living body, to suppress transmission losses in the ultrasonic waves. The thickness of the acoustic matching layer 6 prevents ringing at ¼ of the wavelength λ of the ultrasonic frequency. In general, the acoustic matching layer 6 has a two-layer structure to bring the acoustic impedance gradually closer to that of the living body. The acoustic lens 7 is curved in the longitudinal direction of the piezoelectric elements 1 (the short-axis direction of the ultrasonic probe), as shown in FIG. 4B, to focus the ultrasonic waves in the longitudinal direction at a position based on that curvature.

As also shown in FIG. 4B, Japanese Patent Laid-Open Publication No. 3-203290 and Japanese Patent Laid-Open Publication No. 5-244690 discloses that a base for heat dissipation 8 formed of a metal such as aluminum (Al) is provided on the lower surface of the backing member 2 and the entire probe of the above-described configuration is held on this base for heat dissipation 8. In addition, one end of a thermally conductive member formed as a first thin metal plate 9a (of silver) is surface-bonded by means such as electrically conductive adhesive or solder onto on one end of the piezoelectric elements 1 in the longitudinal direction thereof, as shown in FIG. 4B.

Furthermore, the other end of the first thin metal plate 9a is thermally bonded in a similar manner to a second thin metal plate 9b of a material such as copper (Cu) that is bonded to the lower surface and outer peripheral surface of the base for heat dissipation 8 (see FIG. 4A). In accordance with Japanese Patent Laid-Open Publication No. 3-203290, a cable (not shown in the figures) is connected to the base for heat dissipation 8, to ensure that heat is extracted from the base for heat dissipation 8.

This configuration ensures that heat from the piezoelectric elements 1 that is generated during the conversion from an electrical signal to mechanical oscillation is passed to the base for heat dissipation 8 and is then emitted to the exterior by the thermal-transfer wires of the cable. This prevents problems such as a reduction in reliability of the probe due to a lack of strength caused by thermal deterioration of materials, a reduction in quality due to changes in the characteristics, or low-temperature burns to the skin of the living body.

Problems with Prior Art

However, in the prior-art of an ultrasonic probe of the configuration described above, heat transfer occurs from only one end of the first main surface that forms the transceiver surface in each piezoelectric element 1. In other words, since heat transfer is through the first thin metal plate 9a that is in contact with only one end of the first main surface, heat is not transferred satisfactorily from the center of each piezoelectric element 1 towards the other end thereof.

In such a case, there is some heat transfer to the one end of the piezoelectric elements 1 by the ground electrodes 3a formed of gold (Au) by means such as sputtering, but the electrode thickness is extremely small, on the order of approximately 10 nm. In addition, if the ground electrodes 3a have been formed of silver (Ag), glass is mixed therein in order to obtain sufficient adhesive strength, so that the thermal conductivity thereof is reduced. In either case, sufficient heat transfer cannot be achieved.

Since Japanese Patent Laid-Open Publication No. 5-244690 and Japanese Patent Laid-Open Publication No. 3-203290 also disclose that heat transfer is from only one main surface of the piezoelectric elements 1, this point also demonstrates that heat can not transferred satisfactorily from the piezoelectric elements 1. From this it is clear that the heat generated in each piezoelectric element 1 during the electrical-mechanical conversion is retained, leading to a problem of adverse effects around components such as the acoustic matching layer 6 and the adhesive.

The present invention was devised in the light of the above problems, with the objective of providing an ultrasonic probe in which heat generated within the piezoelectric elements during the electrical-mechanical conversion is transferred satisfactorily and is dissipated to the exterior, suppressing any rise in temperature of the piezoelectric elements.

SUMMARY OF THE INVENTION

The present invention relates to an ultrasonic probe provided with a piezoelectric element for ultrasonic generation that has drive electrodes formed on two main surfaces thereof; an acoustic matching layer formed on the first main surface side of the piezoelectric element; a backing member attached to the second main surface side of the piezoelectric element; a base for heat dissipation provided on a lower surface of the backing member; and a thin metal plate for heat transfer that is thermally bonded between at least one of the main surfaces of the piezoelectric element and the base for heat dissipation; wherein the thin metal plate for heat transfer is surface-bonded to extend from one end of the piezoelectric element over the center thereof toward the other end.
Effects of the Invention Since the above-described configuration ensures that the thin metal plate that acts as an electrode lead is thermally conductive and is in contact with the piezoelectric element from one end thereof toward the other end, further than the center (in other words, in contact with the piezoelectric element over substantially the entirety thereof), heat generated by the electrical-mechanical conversion can be transferred easily from the piezoelectric element.

With the present invention, the thin metal plate for heat transfer is surface-bonded to the first main surface side of the piezoelectric element. This ensures that the thin metal plate transfers heat from the first main surface side of the piezoelectric element that is in contact with the living body, thus enabling an increase in safety with respect to problems such as low-temperature burns during the medical examination.

In addition, the another thin metal plate for heat transfer in accordance with the present invention is surface-bonded to the second main surface side of the piezoelectric element to also act as a lead for the drive electrode, and that thin metal plate is thermally bonded to the base for heat dissipation with an electrically insulating but thermally conductive member therebetween. Since the thin metal plate that acts as an electrode lead is thermally bonded to the base for heat dissipation with an electrically insulating but thermally conductive member, that thin metal plate can also be used for transferring heat.

Furthermore, the thin metal plate for heat transfer of the present invention is surface-bonded to the first main surface side of the piezoelectric element and is thermally bonded to the base for heat dissipation, and also the another thin metal plate for heat transfer is surface-bonded to the second main surface side of the piezoelectric element to also act as an electrode lead for the drive electrode, and is similarly thermally bonded to the base for heat dissipation with an electrically insulating but thermally conductive member therebetween. Since thin metal plates are connected to both main surface sides of each piezoelectric element in this case, the heat of the piezoelectric oscillator is transferred from both main surface sides thereof, further increasing the heat transfer effect.

Even further, the thin metal plate for heat transfer in accordance with the present invention is assumed to have a thickness that is no more than $\frac{1}{20}$ of the wavelength $\lambda$ of the ultrasonic frequency emitted from the piezoelectric element. In this case, even though the thin metal plate is provided over the entirety of the first main surface side of the piezoelectric element that is the transceiver surface side thereof, by way of example, it is of a thickness that can be ignored with respect to the wavelength of the ultrasonic waves, and thus there are no transmission losses in the ultrasonic output. Note that the thickness of the acoustic matching layer is set overall to be $\frac{1}{4}$ of the wavelength $\lambda$ of the ultrasonic frequency, from such considerations.

In addition, even though a thin metal plate is also provided on the second main surface side of the piezoelectric element, the thickness of that thin metal plate is such as can be ignored with respect to the wavelength of the ultrasonic waves, and thus the ultrasonic waves can penetrate the thin metal plate with no reflections therefrom. This does not impede the effect of the backing member in restraining ultrasonic reflection dues to causes such as scattering or absorption.

BRIEF DESCRIPTION OF THE DRAWINGS

FIG. 2 is illustrative of a second embodiment of the ultrasonic probe in accordance with the present invention, where

FIG. 4 is illustrative of a prior-art of an ultrasonic probe, where

DETAILED DESCRIPTION OF PREFERRED EMBODIMENTS

First Embodiment

Figure 1:
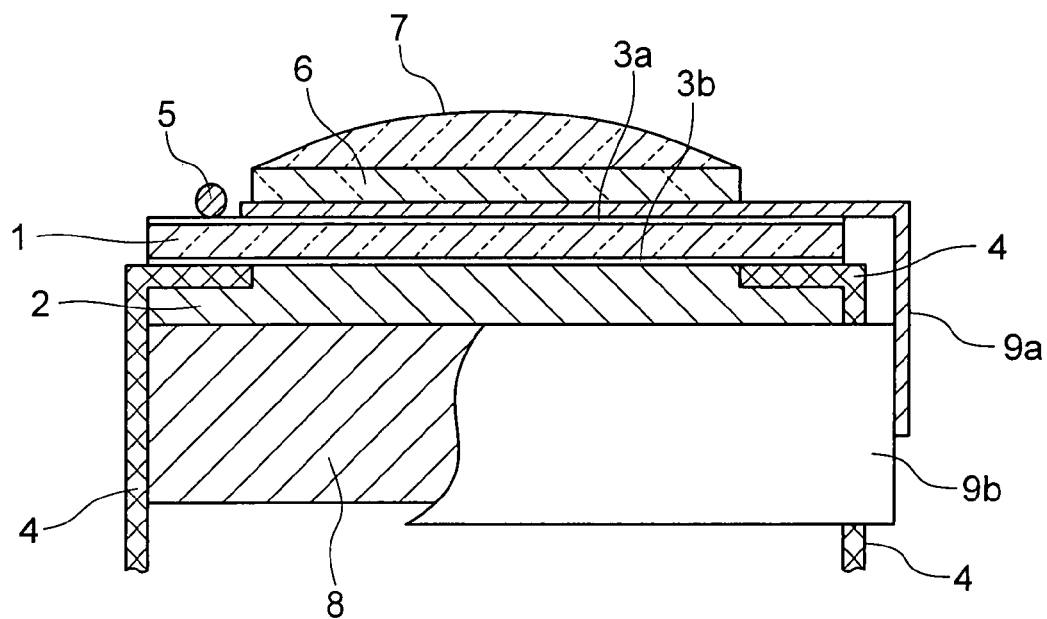
FIG. 1 is a sectional view along the short-axis direction of a first embodiment of the ultrasonic probe in accordance with the present invention.

FIG. 1 is a partially cutaway section taken along the short-axis direction of a first embodiment of the ultrasonic probe of the present invention, with the case thereof removed.

In this ultrasonic probe, piezoelectric elements 1 having ground electrodes 3a and signal electrodes 3b on two main surfaces thereof are affixed to a backing member 2, and an acoustic matching layer 6 and a acoustic lens 7 are provided on a transceiver surface that becomes a first main surface of the piezoelectric elements 1. In addition, the signal electrodes 3b of the piezoelectric elements 1 are led out alternately from the two ends thereof by a flexible substrate 4 and the main probe body is provided on a base for heat dissipation 8. In this case, assume that the ultrasonic frequency is 2.0 MHz. The ground electrodes 3a disposed on the first main surface are connected in common by a conducting wire 5 that extends over the piezoelectric elements 1 in the long-axis direction at the second end of the piezoelectric elements 1, by way of example, and are also connected to a ground path (not shown in the figure) of the flexible substrate 4.

In this first embodiment, a first thin metal plate 9a that acts as a thermally conductive member is provided from one end of the first main surface side of each piezoelectric element 1, over the center thereof and towards the other end, passes between the acoustic matching layer 6 and the piezoelectric element 1, and is in contact with a second thin metal plate 9b that surrounds the base for heat dissipation 8. The thickness of the first thin metal plate 9a is approximately 30 μm, which can be assumed to be approximately 1/100 of the wavelength λ of the ultrasonic frequency.

In this first embodiment, after each first thin metal plate 9a is bonded by an electrically conductive adhesive or the like onto a piezoelectric plate (not shown in the figure) affixed to the backing member 2, by way of example, it is cut away and separated integrally with that piezoelectric plate. This ensures the first thin metal plate 9a is provided individually for each of the piezoelectric elements 1. Subsequently, after the grooves S left by the separation of the plates are filled with a filler material, the acoustic matching layer 6 is formed as a two-layer structure by coating or pasting.

The above-described configuration ensures that each first thin metal plate 9a for heat transfer is in contact with the corresponding piezoelectric element 1 from one end thereof toward the other end past the center thereof, virtually over the entirety thereof, and is thermally bonded to the piezoelectric element 1. This ensures that the heat generated in the piezoelectric element 1 by the electrical-mechanical conversion is transferred easily and thus that heat can be dissipated to the base for heat dissipation 8 through the second thin metal plate 9b. In addition, the first thin metal plate 9a transfers heat from the first main surface side of the piezoelectric element 1 that is in contact with the human body. This enables an increase in safety during medical examinations, particularly with respect to low-temperature burns.

Since the thickness of the first thin metal plate 9a of the first embodiment is approximately 30 μm, this thickness is extremely small, even when the thickness of the electrically conductive adhesive is included. Since it is difficult for the ultrasonic waves to penetrate during transmission, transmission losses can be ignored. The ultrasonic frequency used in this first embodiment is a low frequency of 2.0 MHz, so the thickness of the first thin metal plate 9a is relatively small.

Note that if the thickness of the first thin metal plate 9a is less than 1/20 of the wavelength λ of the ultrasonic frequency, transmission losses can be ignored in practice. This means that if the thickness of the first thin metal plate 9a is within that range, the heat transfer effect is further increased. This point is relevant for the other embodiments as well.

Second Embodiment

Figure 2A:
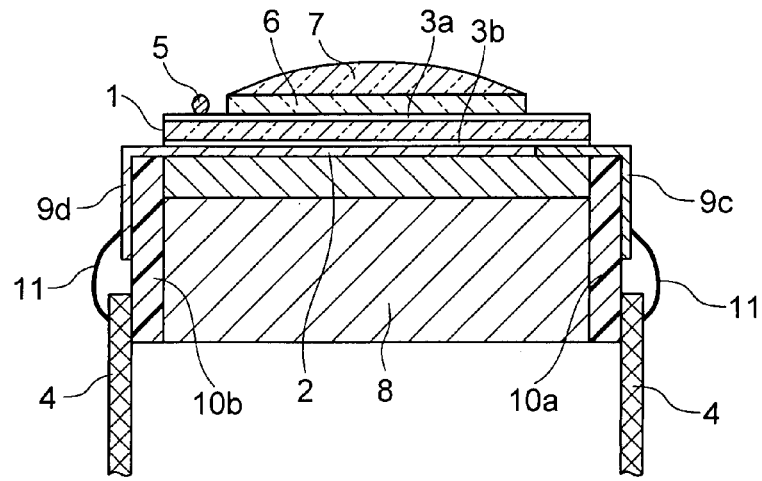
FIG. 2A is a sectional view thereof in the short-axis direction.
Figure 2B:
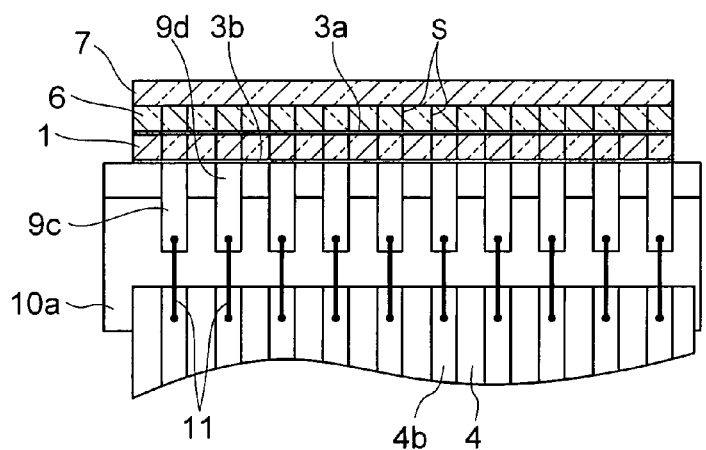
FIG. 2B is a partially cutaway side view thereof in the long-axis direction.
Figure 2C:
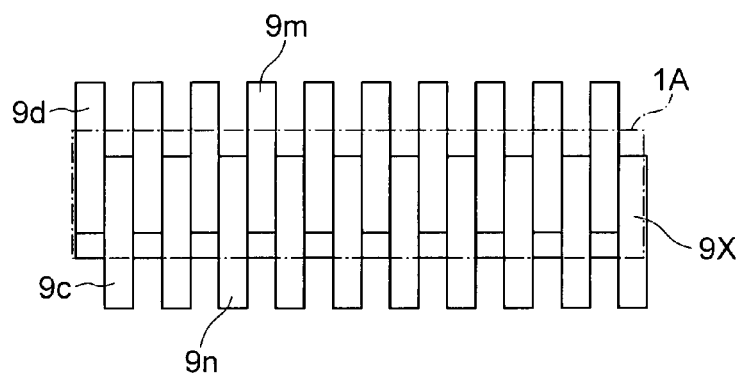
FIG. 2C is a plan view during the fabrication of the thin metal plates.

A second embodiment of the present invention is shown in FIG. 2, where FIG. 2A is a sectional view of the ultrasonic probe in the short-axis direction, FIG. 2B is a partial side view thereof in the long-axis direction, and FIG. 2C is a plan view during the fabrication of the thin metal plates.

With this second embodiment, thin metal plates 9 for thermal conduction are provided on the second main surface side (backing member side) of the piezoelectric elements 1.

In other words, this second embodiment is provided with third thin metal plates 9c at odd-number positions that extend from a first end of the second main surface side of the corresponding piezoelectric elements 1, over the center and towards the second end thereof, and fourth thin metal plates 9d at even-number positions that similarly extend from the second end over the center and towards the first end thereof (see FIG. 2B). The third thin metal plates 9c and fourth thin metal plates 9d extend alternately from the two ends of the piezoelectric elements 1.

Insulating but thermally conductive members such as thermally conductive plates 10a and 10b are bonded by an adhesive to the two side surfaces of the backing member 2 and the base for heat dissipation 8. The third thin metal plates 9c and the fourth thin metal plates 9d that extend alternately from the two ends of the piezoelectric elements 1 are affixed to the upper edges of the thermally conductive plates 10a and 10b. Two edges of the flexible substrate 4 are affixed to the lower edge sides of the thermally conductive plates 10a and 10b. The third thin metal plates 9c and the fourth thin metal plates 9d are connected to signal lines 4b of the flexible substrate 4 by conducting wires 11 formed of silver (Ag).

In this second embodiment, as shown in FIG. 2C that illustrates the process of fabricating the thin metal plates, a thin metal plate 9X from which integrated electrode "fingers" 9 (9m and 9n) extend alternately from the backing member 2 is bonded to the lower surface of a piezoelectric plate 1A by an electrically conductive adhesive or the like, by way of example. The thin metal plate 9X that has been bonded to and integrated with the piezoelectric plate 1A is then affixed onto the backing member 2. The thin metal plate 9X is cut away and separated integrally with piezoelectric plate 1A, to obtain the individual piezoelectric elements 2 and the corresponding thin metal plates 9c and 9d.

This configuration ensures that each of the third thin metal plates 9c and the fourth thin metal plates 9d that are used as electrode leads is in contact with the corresponding piezoelectric element 1 from the first end (or second end) over the center thereof toward the second end (or first end), to provide contact over substantially the entirety thereof (thermal bonding), in a similar manner to the previously described first embodiment. The heat generated in the piezoelectric elements 1 by the electrical-mechanical conversion is thus transferred easily and that heat can be dissipated to the base for heat dissipation 8 through the thermally conductive plates 10.

In this second embodiment, the base for heat dissipation 8 that is made of a metal such as aluminum (Al) is only thermally bonded to the third thin metal plates 9c and fourth thin metal plates 9d with electrically insulating but thermally conductive members (the thermally conductive plates 10) therebetween, so is electrically insulated therefrom. Thus the third thin metal plates 9c and fourth thin metal plates 9d can be used for both leading out the signal electrodes 3b of the piezoelectric elements 1 and transferring heat therefrom.

Third Embodiment

Figure 3:
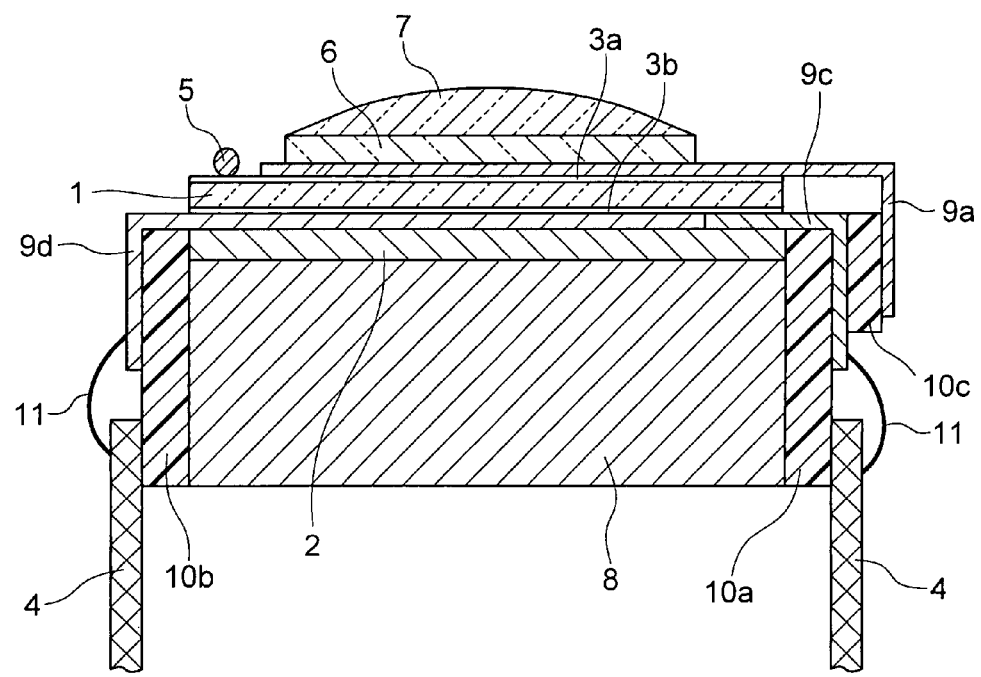
FIG. 3 is a sectional view along the short-axis direction of a third embodiment of the ultrasonic probe of the present invention.
Figure 4A:
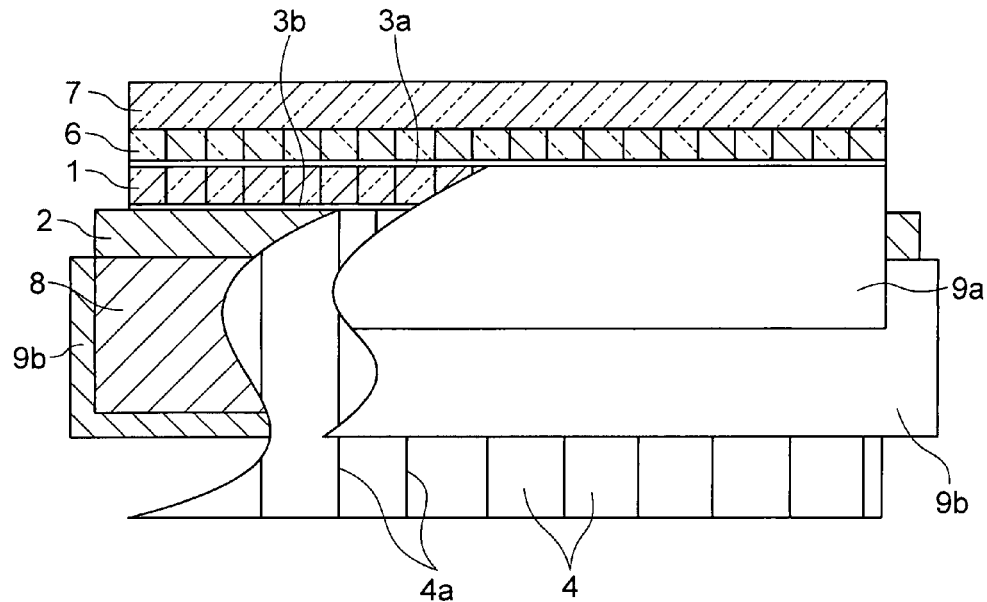
FIG. 4A is a partially cutaway section thereof in the long-axis direction and FIG. 4B is a partially cutaway section thereof in the short-axis direction.
Figure 4B:
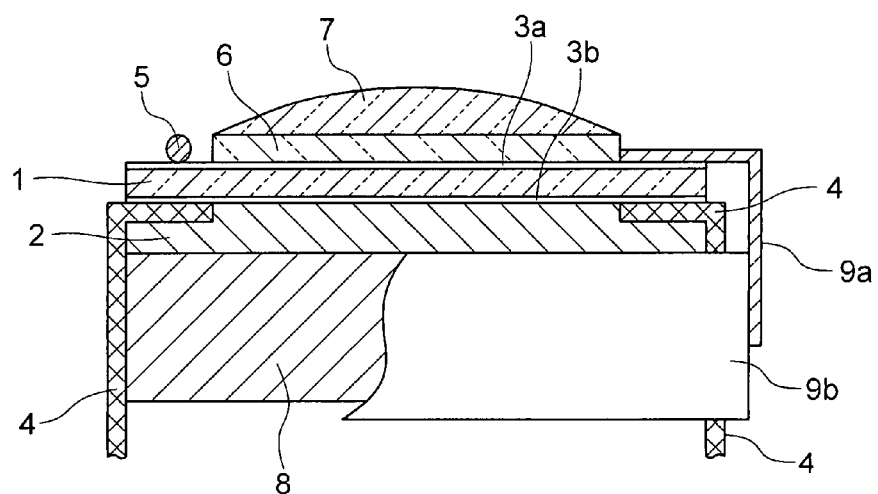

A sectional view along the short-axis direction of a third embodiment of the ultrasonic probe of the present invention is shown in FIG. 3.

In this third embodiment, bent thin metal plates 9a, 9c, and 9d for thermal conductivity are provided on both main surfaces of the piezoelectric elements 1 (the acoustic matching layer side and the backing member side), as shown in FIG. 3. In other words, this third embodiment is similar to the previously described second embodiment in being provided with the third thin metal plates 9c and the fourth thin metal plates 9d that each extend over the second main surface side (the signal electrode 3b side) of the corresponding piezoelectric element 1 from the first end (or second end) over the center thereof toward the second end (or first end).

The third thin metal plates 9c and the fourth thin metal plates 9d extend alternately from the two ends of the piezoelectric elements 1 and are connected to electrically insulating but thermally conductive member (first thermally conductive plates) 10a and 10b on the two side surfaces. In a similar manner to the previously described first embodiment, the first thin metal plate 9a is provided to extend over the first main surface of each piezoelectric element 1 from one end thereof over the center toward the other end. The first thin metal plates 9a are connected to a second thermally conductive plate 10 that is provided attached to bent pieces of the third thin metal plates 9c that extend from the first ends of the corresponding piezoelectric elements.

This configuration ensures that the third thin metal plates 9c and the fourth thin metal plates 9d are thermally bonded over the entirety of the second main surface side of the corresponding piezoelectric elements 1, in a similar manner to the previously described second embodiment, so that generated heat is transferred through the first thermally conductive plates 10a and 10b to the base for heat dissipation 8. In addition, the first thin metal plates 9a are bonded over the entirety of the first main surface side of the corresponding piezoelectric elements 1, enabling heat transfer through the thermally conductive plates 10a, 10b, and 10c to the base for heat dissipation 8.

Since the heat generated by the piezoelectric elements 1 during the electrical-mechanical conversion is therefore transferred by the thin metal plates 9a, 9c, and 9d that are bonded over the entirety of both main surface sides of the piezoelectric elements 1, the heat transfer (heat dissipation) effect with respect to the base for heat dissipation 8 is further increased.

In the above-described embodiments, the signal electrodes 3b of the piezoelectric elements 1 are led out alternately from the two ends of the piezoelectric elements 1, but they could equally well be led out from just one end thereof. In such a case, since the thin metal plate 9a on the first main surface side is the ground potential surface for that piezoelectric element 1, it can be connected directly to the base for heat dissipation 8. In addition, an electrically insulating but thermally conductive member is used for the thermally conductive plate 10 is used in this embodiment, but it could equally well be an electrically insulating but thermally conductive adhesive.

What is claimed is:

1. A thermally enhanced ultrasonic probe comprising:
    a piezoelectric element for ultrasonic generation comprising a ground electrode forming a first main surface and a signal electrode forming a second main surface thereof;
    an acoustic matching layer formed on the first main surface of said piezoelectric element and electrically bonded to the ground electrode;
    a backing member formed on the second main surface of said piezoelectric element and electrically bonded to the signal electrode;
    a base for heat dissipation provided on a surface of the backing member which is opposed from the second main surface of said piezoelectric element; and
    a thin metal plate for heat transfer that thermally bonds at least one of the first main surface and the second main surface of said piezoelectric element and said base for heat dissipation;
    wherein said thin metal plate for heat transfer is thermally bonded to at least one of the main surfaces of said piezoelectric element and wherein said thin metal plate extends from one end of said piezoelectric element over a center thereof toward another end, such that said thin metal plate is in contact with said piezoelectric element over substantially the entire surface area of said piezoelectric element; and
    wherein said thin metal plate for heat transfer is thermally bonded to said first main surface of said piezoelectric element and is thermally bonded to said base for heat dissipation, and also another thin metal plate for heat transfer is thermally bonded to said second main surface of said piezoelectric element and extended from two ends of the piezoelectric element to act as an electrode lead for said signal electrode, and is thermally bonded to said base for heat dissipation with an electrically insulating but thermally conductive member there between wherein said thin metal plate is electrically bonded to a substrate via at least one signal line.

2. The thermally enhanced ultrasonic probe according to claim 1, wherein said thin metal plate for heat transfer is surface-bonded to the ground electrode layer of said piezoelectric element.

3. The thermally enhanced ultrasonic probe according to claim 2, wherein said thin metal plate for heat transfer has a thickness that is no more than $1/20$ of the wavelength $\lambda$ of the ultrasonic frequency radiating from said piezoelectric element.

4. The thermally enhanced ultrasonic probe according to claim 1, wherein said thin metal plate for heat transfer is surface-bonded to the signal electrode layer of said piezoelectric element to lead out said signal electrode.

5. The thermally enhanced ultrasonic probe according to claim 4, wherein said thin metal plate for heat transfer has a thickness that is no more than $1/20$ of the wavelength $\lambda$ of the ultrasonic frequency radiating from said piezoelectric element.

6. The thermally enhanced ultrasonic probe according to claim 1, wherein said thin metal plate for heat transfer has a thickness that is no more than $1/20$ of the wavelength $\lambda$ of the ultrasonic frequency radiating from said piezoelectric element.

* * * * *